United States Patent [19]

Hutchinson, Jr.

[11] 4,009,004

[45] Feb. 22, 1977

[54] REAGENT AND METHOD FOR DETERMINATION OF PHOSPHOROUS

[76] Inventor: Marvin E. Hutchinson, Jr., 5020 Palmetto Way, Pacifica, Calif. 94044

[22] Filed: May 17, 1976

[21] Appl. No.: 687,354

[52] U.S. Cl. .............................. 23/230 B; 252/408
[51] Int. Cl.² ................. G01N 31/22; G01N 33/16
[58] Field of Search ................... 23/230 B; 252/408

[56] References Cited

UNITED STATES PATENTS

| | | | |
|---|---|---|---|
| 3,547,586 | 12/1970 | Denney | 23/230 B |
| 3,795,484 | 3/1974 | Daly et al. | 23/230 B |
| 3,874,853 | 4/1975 | Byrnes | 23/230 B |
| 3,926,735 | 12/1975 | Monte et al. | 23/230 B X |

Primary Examiner—Robert M. Reese
Attorney, Agent, or Firm—Mark C. Jacobs

[57] ABSTRACT

A method and reagent for the determination of inorganic phosphate in biological fluids by the reduction of molybdenumphosphate with a reducing agent, a non-ionic lineating surfactant, an acid, and optionally polyvinylpyrrolidone (PVP), wherein the sample used in the test method need not be protein free.

18 Claims, No Drawings

REAGENT AND METHOD FOR DETERMINATION OF PHOSPHOROUS

BACKGROUND OF THE INVENTION

1. Field of Invention

This invention relates to a new reagent for use in a new method for the determination of inorganic phosphate in biological fluids, which have or have not been made protein free, by the use of a reducing agent selected from the group consisting of ferric ammonium sulfate (FAS) stannous chloride, and ascorbic acid, in the presence of a lineating surfactant.

2. Prior Art

It is known to the art to reduce molybdenum phosphates to molybdenum blue. Various methods and the reducing agents used therein have been discussed by Henry in *Clinical Chemistry*, (Harper & row, 1968).

The patent literature also discusses such processes. Thus Daly et al in U.S. Pat. No. 3,795,484 disclose an automated method for the determination of inorganic phosphate in serum. However at column 2 line 19 it specifically states that a protein free serum sample is required for the test.

U.S. Pat. No. 3,547,586 discloses the use of PVP to speedup the formation of yellowish phospho-molybdate prior to the reduction step. Set forth therein also is a synopsis of the Hycel Inc. determination which does not require protein precipitation, but which is slow, 35 minutes, and fails to obey the Beer-Lambert Law. The Hycel procedure also suffers from the fact that glucose levels above 200mg. percent interfere with the test, and since the test is often desired for diabetics, there is limited utility since diabetics are excluded from its use. Note also that the Hycel reactant is stable for about 1 year, provided that it is refrigerated.

A very recent patent is the one to Morin & Prox, 3,853,469 which uses ortho-phenylenediamine or a salt thereof with an acid as the reducing system, with or without a dipolar aprotic solvent as a catalyst, with or without PVP in a molybdate method.

Morin and Prox in column 1 that the art recognizes that ferrous ammonium sulfate, stannous chloride and ascorbic acid have all been utilized in molybdate methods but are not considered satisfactory for several reasons. Stannous chloride is unstable, deviates from the Beer-Lambert law, has a sensitivity to change in acidity and has unstable color results, while FAS and ascorbic acid, while they obey the Beer-Lambert law, are slow acting and lack sensitivity. Slow reaction is stated to be at least 30 min.

It is concluded that the ideal molybdate system would have a reducing agent that is stable, acts in about 5 minutes, follows Beer's law, and produces stable color among its attributes.

DESCRIPTION OF THE INVENTION

The system described herein has all of the attributes listed above for the ideal system, and in addition is easy to utilize, has an extended shelf life without refrigeration, and is cost competitive.

It is a prime object therefore to provide a new direct method for the determination of inorganic phosphorous by a molybdate reduction system.

Another object is to provide a stable reducing agent which does not require refrigeration.

Yet another object is to provide a reaction which can be carried out without the need for removing protein from the sample.

A further object is to provide a determination method that takes only about 5 minutes to give true and accurate results.

A still further object is to provide a technique which follows the Beer-Lambert law and is cost competitive.

A yet further object is to provide a new reducing agent composition for use in a molybdate test for inorganic phosphorous.

Other objects are recited herein and others will be obvious from a reading of the balance of this specification.

In brief, the invention relates to the provision of a new reducing agent composition, and the method employing same for the determination of inorganic phosphorous in body fluids, which need not have had the protein removed therefrom.

The reagent composition comprises 0.001% to 20% of an acid; .01% to 10% gram percent of a molybdate salt, 0.001% to 10% of a reducing agent selected from the group consisting of FAS, $SnCl_2$, and ascorbic acid, 0.001% to 10% of a nonionic lineating surfactant, and optionally PVP. The term lineating surfactant is intended to mean a surfactant that allows a linear progression of color to occur, which obeys the Beer-Lambert law. The ratio of fluid to reagent is between 1:300 and 1:15.

It is believed that this invention represents a unique improvement over the prior art. While the use of a surfactant in combination with PVP is known, for use as a clarifying agent, as per Morin and Prox supra, with their preferred surfactant being Triton X-100, as will be seen in detail later in this application unsatisfactory results are obtained where this combination is utilized for applicant's intended purpose. Accordingly, Triton X-100 is not classified as a lineating surfactant.

It has now been found that the reducing agents selected from the group consisting of FAS, $SnCl_2$ & ascorbic acid when used in an acid solution with a lineating surfactant, provide a superior reducing system of phosphomolybdate to molybdenum blue, in that the Beer-Lambert law is obeyed, ambient temperature is used stable color is produced, and the reaction takes only about 5 minutes when such systems are employed. This is quite surprising in view of the prior knowledge concerning these reducing agents, as per Hycel's mode and other information.

The PVP plays the role of the catalyst, in that it allows the reaction time to be reduced from 25–30 minutes to about 5 minutes.

The invention includes the method of determining inorganic phosphate in biological fluids. Fluids such as serum, plasma, urine and spinal fluid may be tested without the need for the removal of of protein. They may be fluids of animals or humans. Upon mixing of the fluid with the reduction system of this invention, an intense stable blue color will develop in linear proportion to the phosphate content of the sample of fluid.

While not being bound to any particular theory, it is believed that the blue color results from the formation of complexes, as a result of the reaction of phosphate ions with molybdic acid in the presence of a strong acid such as sulfuric, to form phohosphomolybdic acid, which is subsequently reduced by the FAS, $SnCl_2$ or ascorbic acid to the blue complexes.

Possible Reaction

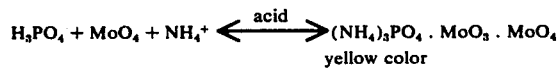
yellow color

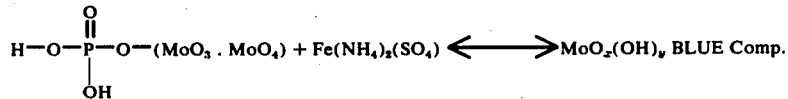 BLUE Comp.

wherein $x$ is average oxidation state ranging from 2.0 to 2.5; $y$ is an average oxidation state ranging from 0.05 to 2.0

The average oxidation state for Mo ranges from 5.00 to 5.70

In the reducing compositions of this invention, any phosphate free molybdic ion source can be employed. Molybdic acid, as well as molybdate salts such as those of Cd,Ba,Bi,Pb,Ca,K,Na,Zn and the like can be employeed. The molybdenum ion source is employed in an amount of from 0.001% to 5% based on the total weight of the composition. The source used must be a soluble salt. Heteromolybdates, as defined in the Condensed Chemical Dictionary, and the Edition by Van Nortrand can also be employed, such as those of Al,Cr,Fe,Se,Ni, and the like. Soluble molybdenum complexes as with cobalt may also be used.

The acid that is preferred is sulfuric acid. Other useful acids include picric, butyric, oxalic, acetic, benzoic, formic, maleic, tartaric and the like. If protein has been removed, then HCl can be used. Sulfurous acid is not acceptable as precipitates will tend to form. The utility of nitric acid has not been determined at this time. Acid is employed in an amount of from 0.001 to 20% based on total weight.

With respect to the surfactant, not all surfactants that are non-ionic can be employed in this invention. The surfactant must act as lineating ingredient to allow a linear progression of color to occur. The surfactant also must prevent any protein present from precipitating. Triton X-100, a very commonly used surfactant was found not to have the desired properties. An example of a lineating surfactant, is polyoxyethylene 10 oleyolether. Other suitable surfactants include tergitol TP-9 and Tergitol 15-S-9.

While the operable surfactants have been designated as lineating surfactants due to their effect on color, such surfactants must also possess acid stability, must not precipitate protein, nor permit the reagent system to deteriorate in a short period of time.

Accordingly, Aerosol 122, Ultrawet 60L, Levor IV, Sigma surfactant, Isoterg, several of the TWEENS, and several of the BRIJ brand nonyl-phenylpolyethylene glycol esters were tried singly and in combinations and were rejected due to protein precipitation, non-linearity, short shelf life, or undesired side reactivity. Those found acceptable are employed in an amount of from 0.001% to 10% based on total weight.

The reagent systems of this invention are formulated as aqueous solutions.

Any suitable colorimeter or spectrophotometer can be used to measure the absorbance. Examples include the Coleman Perkin Elmer Model 124, the direct reading instrument of Kiess as per U.S. Pat. No. 3,561,878, and the like. After a suitable recalibration, the instrumentation of Hycel, American Monitor, Abbott, and Technicon can be employed to carry out the method of this invention.

The preferred PVP is of the order of 10,000 mol. wt. Useful materials are available in the range of about 10K to 60K mol. wt. Over about 60K the product is either partly or totally insoluble. Mol. Wts. under 9000 are not readily available. However no reason is seen for their unacceptability. When employed, the PVP is used in an amount of from 0.0001% to 10%. It has been found that the PVP aids in speeding up the measurement capability and contributes somewhat to the linearity of the reaction. The suitability of PVP as a catalyst is unobvious, in that previously it has been employed as a clarifier. Note specifically the Morin and Prox patent, 3,853,469.

The following examples illustrate the preparation of the novel reagent of this application and the method of its use, but these examples should not be considered in a limiting sense.

EXAMPLE I

Ammonium molybdate, 2.20 grams was dissolved in about 25ml of deionized water. 18 ml. of conc. $H_2SO_4$ was added and the mixture was cooled to room temperature, and set aside as Solution A.

FAS, 4.00 gms was dissolved in 25 ml $H_2O$, followed by the addition of 10 ml of conc. $H_2SO_4$ and the solution was cooled to room temperature and designated Solution B.

Polyoxyethylene 10 Oleylether, 100 ml is dissolved in 800 ml of water with gentle heating not over 56° C followed by the addition of sufficient water to bring the volume to 1000 ml. This is designated as Solution C.

EXAMPLE II

Solutions A and B are mixed and 300 ml of water are added and then 40 ml of Solution C is added. The solution is then brought to a volume of 1000 ml by the addition of deionized water.

A portion of this was stored for over one year in a room where the temperature varied by season between 15° and 30°, and was found to be stable.

Since Solution C's material is prone to bacterial contamination, storage in a temperature controlled room is recommended. Refrigeration where the temperature drops below 4° C will cause the reagent to form a precipitate which can be redissolved by heating the reagent to 40° C for 30 minutes. No apparent damage to the reagent was observed.

EXAMPLE III

A portion of the product of Example II, prior to storage had a quantity of 0.25 gms per liter of PVP added thereto. This was stored at ambient temperature and after three (3) months it was tested and found to be stable.

EXAMPLE IV

A reduction reagent was prepared in the manner of Example II but 5.00 grams of sodium molybdate were substituted for the ammonium molybdate. Similar results were obtained as when the ammonium salt was used.

EXAMPLE V

A reduction reagent was prepared in the manner of Example II but $SnCl_2$, 1.93 grams was utilized in place of FAS for Solution B. Stability was found to exist only for 10 to 15 days.

EXAMPLE VI 1.80 grams of ascorbic acid was substituted for the FAS of Example I in the preparation of a reagent system of this invention. Reduction occurs immediately, and thus ascorbic acid cannot be employed in this process.

EXAMPLE VII

The Polyoxyethylene 10 Oleylether was replaced by both of Tergitol TP-9 and Tergitol 15-S-9 in Solution C to prepare a product by the method of Example II. The results were deemed acceptable when the product was employed in the instant test.

EXAMPLE VIII

To the reagent system of Example V was added 0.5 gm of PVP immediately prior to its utilization in the method of this invention. It was tested and found stable and acceptable for use.

EXAMPLE IX

A reagent system was prepared by the technique of Example II, utilizing sulfuric acid, in the amount of 18 ml., and 5.00 grams sodium molybdate for Solution A; 1.93 grams of $SnCl_2$ and 10 ml. of the same acid for Solution B; and 40 ml of Tergitol TP-9 and Tergitol 15-S-9 for Solution C. Satisfactory results were obtained, but shelf life was short. Tergitol is a registered trademark of Union Carbide Corporation.

The procedure for the analysis of the specimens for phosphate involves the use of a known phosphorous standard. A set of standard solutions are prepared and made to contain 1,2,3,4,5,6,7,8,9,10,14 and 20 mg/dl organic phosphate.

To A series of tubes is added, .05 ml of each of the standard phosphate solutions and also a reagent blank tube containing .05 ml $H_2O$ or a solution containing 0 mg/dl phosphate.

To another tube is added, .05 ml an unknown sample, as many unknown samples may be run as necessary, which are either human, animal or aqueous.

3.0 ml the reagent system is added to each tube. Timed sequence is not important in that the reaction is virtually complete at the end of the incubation period.

The color reaction is allowed to develop for 5 to 7 minutes at room temperature (25° C). The tubes are then read against the blank for absorbance at 650 nm on a colorimeter or spectrophotometer.

It is found that there is a linear proportion between the absorbance and the phosphate concentration.

It is also to be seen that since the instant reagent system has a maximum absorbance peak at 650 nm, and this is a very broad peak, accurate readings can also be made at from about 400 nm to 800 nm.

EXAMPLE X

When the procedure above was utilized with the reagent system of Example III (PVP included) within about 6 minutes a blue color developed in the phosphate specimen at room temperature and is stable for over 3 hours. A reading was made on the colorimeter and was found linear.

EXAMPLE XI

When the technique was repeated but using the reagent of Example II (no PVP), while there was no cloud in the serum, the reaction was not complete until about 20 minutes, and it too was found to be linear.

EXAMPLE XII

When the procedure was utilized with a reagent that omitted Solution C, but did contain PVP, the color developed, and the reaction was linear and stable, but took 20 minutes.

EXAMPLE XIII

When Triton X-100 was used in the formulation of Solution C and the reagent employed in the technique, the solution precipitated, turned blue, and was not suitable for analysis.

EXAMPLE XIV

When reagent systems of this invention based on stannous chloride are employed with the technique above, it is found that a deep blue color of a different intensity develops that is found linear and stable on testing.

It was found that as the amount of PVP was increased, the total reaction time was decreased, up to 0.25 gms. no decrease in time after that amount. It was determined that the use of 0.25 gms. PVP gave rise to reactions that could be visibly determined to be complete in 5 to 7 minutes.

It is known that the normal adult level of inorganic phosphorous is 2.5 to 4.5 mg per deciliter of body fluid, and for infants, the normal level is 3.5 to about 7 mg/deciliter. Accurate measurements were made using the 7 minute reagent systems on equipment made by Hycel, American Monitor, Abbott Labs., Chemetrics. In contrast to the generally acceptable Hycel technique, which requires 7 minutes of preparation and 30 minutes of incubation, the present method requires the same 7 minutes of preparation but only about 5 minutes of incubation. Even when PVP was omitted, operation time was only 20 to 25 minutes.

Since the reagents of this invention have long shelf life, large quantities can be prepared at lower cost and with appropriate lessening of the chance of error. The single reagent system of this invention is seen to permit the laboratory to increase the amount of work output in a given day over the prior art modes.

Other advantages to the instant technique include increased sensitivity, the requirement of a smaller sample, and an increase in linear response of greater than 20 mg% phosphate. Whereas usually 0.1 ml of sample to 3.0 ml reagent is employed, due to sensitivity of the instant test, only about ½ that amount is needed here.

As indicated previously, when plasma and urine are tested for phosphorous by the instant method linear stable results are obtained.

On the point of stability it is seen that the product of Hycel, if kept under refrigeration, has a shelf life of about 9 months, whereas the instant product line is stable at ambient temperature for at least one year. Other reagent systems employ multiple components and are therefore not comparable.

One further advantage of the instant system is the fact that less acid is employed than in prior art tests, that of Prox for example. This is an important benefit, in that organic phosphates give falsely elevated results in high acidic conditions due to hydrolysis of the phosphates. The final acidity in the Prox patent is 4.0% while the acidity of this reagent is 2.8%. Thus, the instant system tends to have less interference from the hydrolysis problem. Hycel has a concentration of 5.32% acid in their reagent which creates a large problem of interference with the test, but their test will not be operative with a lesser amount of acid.

Since certain changes may be made in the above method and reagent composition without departing from the scope of the invention herein involved, it is intended that all matter contained in the above description shall be interpreted as illustrative and not in a limiting sense.

What is claimed is:
1. A reagent for determining inorganic phosphate in biological fluid which comprises an aqueous solution of a reducing agent,
.001 to 20% an acid
.001 to 5% Molybdate ion
.001 to 10% a lineating surfactant.
2. The reagent of claim 1 wherein the acid is concentrated sulfuric acid.
3. The reagent of claim 1 further including PVP.
4. The reagent of claim 3 wherein the PVP content is from 0.0001% to about 10% of the composition.
5. A method for determining the inorganic phosphates in biological fluids which comprises admixing a sample of biological fluid with the reagent of claim 1, wherein the ratio of fluid to reagent is between 1:300 and 1:15, and determining the concentration of inorganic phosphate by measuring the absorbance.
6. The method of claim 5 wherein the reagent further includes PVP therein.
7. The method of claim 5 wherein the reagent admixed with the biological fluid comprises an aqueous solution of ferric ammonium sulfate, molybdate ion, concentrated sulfuric acid and a lineating surfactant.
8. The method of claim 7 wherein the lineating surfactant is polyoxyethylene ether 10 oleyol.
9. The reagent of claim 1 wherein the reducing agent is selected from the group consisting of ferric ammonium sulfate, stannous chloride.
10. The reagent of claim 9 further including PVP having an average molecular weight of about 10,000 to about 60,000.
11. The reagent of claim 10 wherein the lineating surfactant is polyoxyethylene ether-10 oleyol.
12. The reagent of claim 11 wherein the reducing agent is ferric ammonium sulfate.
13. The reagent of claim 11 wherein the acid is concentrated sulfuric.
14. The reagent of claim 13 wherein the molybdate ion is derived from molybdic acid.
15. A method of determining phosphate content in serum without removing the protein content therein which comprises admixing a sample of the serum with a reagent comprising ammonium salt of molybdic acid, ferric ammonium sulfate, an acid and a lineating surfactant, and measuring the absorbance on a colorimeter or spectrophotometer.
16. The method of claim 15 wherein the ferric ammonium sulfate is replaced by stannous chloride.
17. The method of claim 15 wherein the reagent further includes PVP therein.
18. The method of claim 17 wherein the acid is concentrated sulfuric and the lineating surfactant is polyoxyethylene ether-10 Oleyol.

* * * * *